United States Patent
Albertorio et al.

(10) Patent No.: US 8,083,803 B2
(45) Date of Patent: Dec. 27, 2011

(54) ARTHROSCOPIC UNICOMPARTMENTAL KNEE TECHNIQUE AND INSTRUMENTATION

(75) Inventors: Ricardo Albertorio, Naples, FL (US); Ronald C. Iannarone, Aiken, SC (US); Jacob A. Jolly, Naples, FL (US); David Koogle, Naples, FL (US); Jerry Sterrett, Naples, FL (US); Reinhold Schmieding, Naples, FL (US); Scott Sherman, Naples, FL (US)

(73) Assignee: Arthrex, Inc., Naples, FL (US)

( * ) Notice: Subject to any disclaimer, the term of this patent is extended or adjusted under 35 U.S.C. 154(b) by 905 days.

(21) Appl. No.: 12/149,614

(22) Filed: May 5, 2008

(65) Prior Publication Data

US 2008/0275512 A1    Nov. 6, 2008

Related U.S. Application Data

(60) Provisional application No. 60/915,800, filed on May 3, 2007.

(51) Int. Cl.
*A61F 2/38* (2006.01)
*A61B 17/58* (2006.01)

(52) U.S. Cl. ......... 623/20.3; 623/20.21; 606/88; 606/96

(58) Field of Classification Search ............... 606/80, 606/86 R, 87, 88, 96; 623/20.21, 20.23, 623/20.3, 20.31
See application file for complete search history.

(56) References Cited

U.S. PATENT DOCUMENTS

| | | | |
|---|---|---|---|
| 5,484,441 A * | 1/1996 | Koros et al. | 606/79 |
| 5,520,695 A * | 5/1996 | Luckman | 606/88 |
| 6,716,215 B1 * | 4/2004 | David et al. | 606/80 |
| 7,771,483 B2 * | 8/2010 | Justin et al. | 623/20.34 |
| 7,828,853 B2 * | 11/2010 | Ek et al. | 623/20.32 |
| 2005/0273107 A1 * | 12/2005 | Stevens | 606/73 |
| 2007/0233128 A1 | 10/2007 | Schmieding et al. | |
| 2008/0039852 A1 | 2/2008 | Schmieding et al. | |

* cited by examiner

*Primary Examiner* — Thomas C. Barrett
*Assistant Examiner* — Michael T Schaper
(74) *Attorney, Agent, or Firm* — Dickstein Shapiro LLP (57) ABSTRACT

A method and apparatus for arthroscopic unicompartmental knee surgery which include a femoral component and a tibial component. The femoral component is installed in a trough in the femoral condyle formed by using a template, a plurality of drill pins and a plurality of corresponding cutters. The template is aligned with the curvature of the femoral condyle, the two drill pins are passed through the template and drilled into the femur, cutters are advanced over the corresponding drill pins to make holes in the femur, and the remaining hourglass shaped bone is removed with osteotomy pliers to form the trough. A tibial socket for the tibial component is formed in a retrograde manner.

7 Claims, 9 Drawing Sheets

ARTHROSCOPIC UNICOMPARTMENTAL KNEE TECHNIQUE AND INSTRUMENTATION

CROSS-REFERENCE TO RELATED APPLICATIONS

This application claims priority to U.S. Provisional Application No. 60/915,800, filed on May 3, 2007, the entire contents of which are hereby incorporated by reference.

BACKGROUND OF THE INVENTION

1. Field of the Invention

The present invention relates to the field of arthroscopic surgery and, more particularly, to methods of reconstructive knee surgery.

2. Description of the Related Art

Partial knee replacement surgery, also called unicompartmental knee arthroplasty, is routinely considered for the treatment of osteoarthritis of the knee joint. Partial knee replacement surgery has generated significant interest because it entails a smaller incision and faster recovery than traditional total joint replacement surgery.

When partial knee replacement is performed, bone and cartilage on the end of a femur and top of a tibia are removed. This is performed using precise instruments to create exact surfaces to accommodate an implant. A knee replacement implant made of various biocompatible materials such as metal or plastic is then placed to function as a new knee joint. Typically, the knee replacement implant includes the following: (i) an arc shaped femoral component which fits into a corresponding trough on the bottom of the femur, and provides a replacement articulating surface for the femur, and (ii) a tibial component which fits into a socket on the tibial plateau and forms a corresponding replacement articulating surface for the tibia. The femoral and tibial components are preferably made of a biocompatible material.

U.S. Patent Application Publication No. 2008/0039852, the disclosure of which is incorporated by reference, describes the use of a dual-sided cutter for forming the femoral trough and tibial socket by retrograde drilling. It would be desirable to provide an alternative technique for easily creating the femoral trough and tibial socket, and using corresponding femoral and tibial components that can be easily and securably fixed in the bone holes.

SUMMARY OF THE INVENTION

The present invention provides an apparatus and method for reconstructive knee surgery, particularly unicompartmental knee surgery, which fulfills the above-noted need. More specifically, the present invention provides a femoral component having an outer surface shaped in the form of a femoral condyle and having two projections extending from the opposite surface for securing the component in the femur. The invention also includes a tibial component formed of a first member with an articular outer surface and a threaded baseplate member configured to be screwed into the tibial plateau, the tibial articular surface being securely engaged to the tibial baseplate. In another embodiment, the tibial component is a single piece member with a projection on its bottom surface for securing the component in a hole in the tibial plateau.

The femoral component is preferably made of cobalt-chrome alloy. In one embodiment, the projections from the femoral component have bullet tips.

The present invention also provides an assembly for forming the femoral trough including a template, a plurality of drill pins and a plurality of corresponding cutters. The assembly is employed to create a femoral trough in a femoral condyle. A cutter, for example, a retrodrill cutter or a flip retrograde cutter is employed to create a tibial socket from outside in, before or after the formation of the femoral trough.

The present invention also provides a method of forming a femoral trough to accept a unicompartmental femoral component. A template is aligned with the curvature of the femoral condyle. Drill pins are inserted through the template and cutters are inserted over the corresponding drill pins. The cutters are then used to drill into the femoral condyle to form an hourglass-shaped trough in the femur. A unique osteotomy plier is then used to remove the excess bone to in order to create an elongated oval shaped trough for the femoral component.

The present invention also provides a method of arthroscopically preparing the femur and the tibia to accept the tibial and femoral components for repairing the articulating surfaces of the femur and tibia. The method includes forming a tibial socket and creating a trough in the femoral condyle, as described above. The tibial and femoral components are then mounted and secured in the tibial socket and the femoral trough, respectively.

Other features and advantages of the invention will become apparent from the following description of the invention, which refers to the accompanying drawings.

DETAILED DESCRIPTION OF THE PREFERRED EMBODIMENT

Referring now to the drawings, where like elements are designated by like reference numerals, FIGS. 1-8 illustrate tibial and femoral components and a method of arthroscopically preparing the tibia and the femur to accept a unicompartmental implant that covers a portion of the contact area between femur and tibia.

Figure 1A:
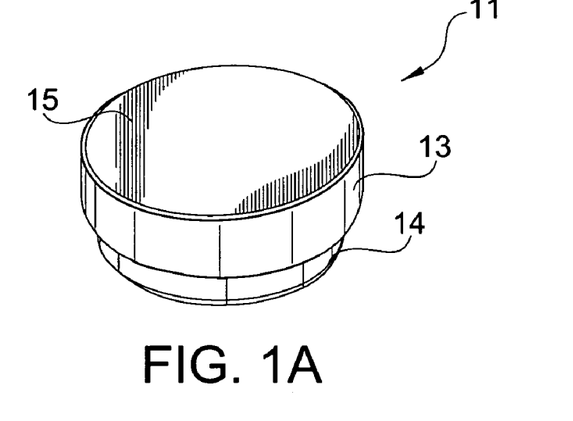
FIG. 1A illustrates a perspective view of a tibial articular surface member according to a first embodiment of the present invention.
Figure 1B:
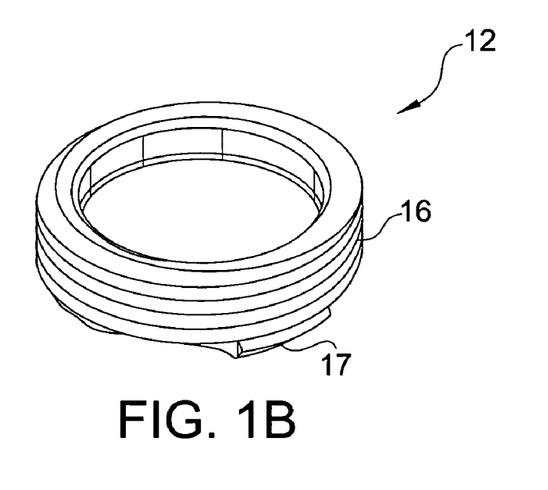
FIG. 1B illustrates a perspective view of a threaded tibial baseplate member according to the first embodiment of the present invention.
Figure 1C:
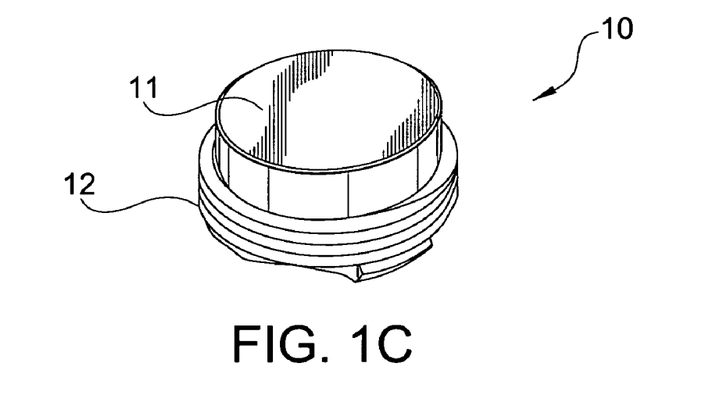
FIG. 1C illustrates a perspective view of the tibial articular surface member and the tibial baseplate member of FIGS. 1A and 1B assembled together to form a tibial component.

Referring to FIGS. 1A-1C, an assembled tibial component 10 includes a tibial articular surface member 11 and a threaded tibial baseplate member 12. The tibial articular surface member 11 is seated on and secured to the threaded tibial baseplate 12. The height of the tibial component 10 is preferably about 7.5 mm.

The tibial articular surface member 11 is formed of a first portion 13 and a second portion 14. The first and second portions 13, 14 are substantially circular in cross section with a diameter of about 10 mm-20 mm. The first portion 13 has a top surface 15 with a slope of preferably about 0°-15° and generally takes the form of a tibial surface. The height of the tibial articular surface member 11 is about 4 mm. The tibial articular surface 11 member is preferably formed of compression molded UHMWPE.

The threaded baseplate member 12 has a first portion 16 and a second portion 17. The threaded baseplate member 12 is preferably about 10 mm to about 20 mm, having a height of about 0.2 inches. The threaded baseplate member 12 is preferably formed of a titanium alloy having an aluminum oxide blast finish. The first portion 16 has threads, preferably having a minor diameter of about 0.394 inches to about 0.787 inches, a pitch of about 0.030 inches. The depth of the thread is preferably about 0.039 inches and the thread angle is about 30°. The second portion 17 has a hex (not shown) on its underside for engagement with a driver such that it can be screwed, in a retrograde manner, into a tibial socket.

Figure 2A:
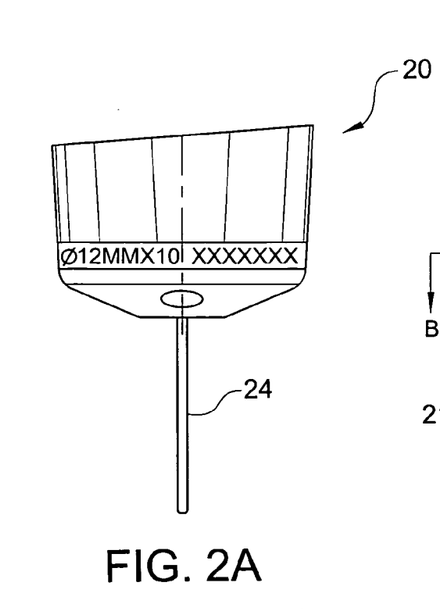
FIGS. 2A-2B illustrate various views of an alternative tibial component of the present invention.
Figure 2B:
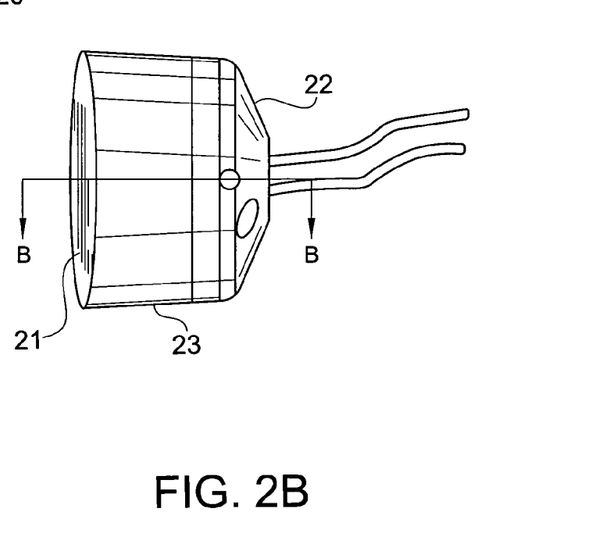

Referring to FIGS. 2A-2B, in another embodiment, a tibial component 20 is provided in a single piece design, and includes a first end 21, a second end 22, and a portion 23 structurally connecting the first and second end 21, 22. The first end 21 is provided in the form of a tibial articulating surface (to match the surface contour of the tibial plateau) and the second end 22 is tapered for insertion into a tibial socket or tunnel drilled into the tibia to accommodate the tibial component 20. A suture 24 or other strand extending from the tapered end 22 is provided to securely engage the tibial component 20 in the tibial socket.

The first and second ends 21, 23 are substantially circular in cross section with a diameter of about 10 mm-16 mm. The surface of the first end 21 has a slope of about 0°-15°. Tibial component 20 is preferably made of cobalt-chrome alloy or of polymer (machined or compression molded).

Figure 3A:
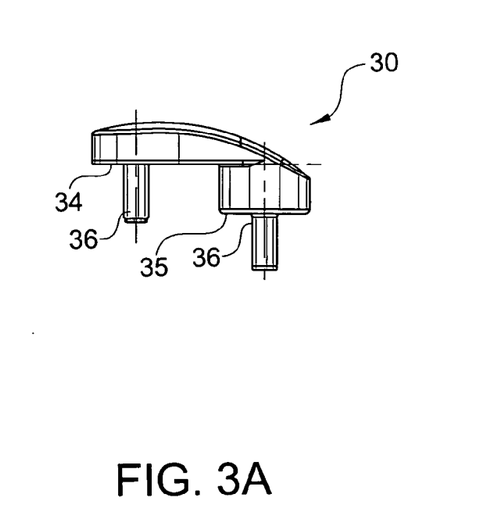
FIGS. 3A-3B illustrate various views of a femoral component of the present invention.
Figure 3B:
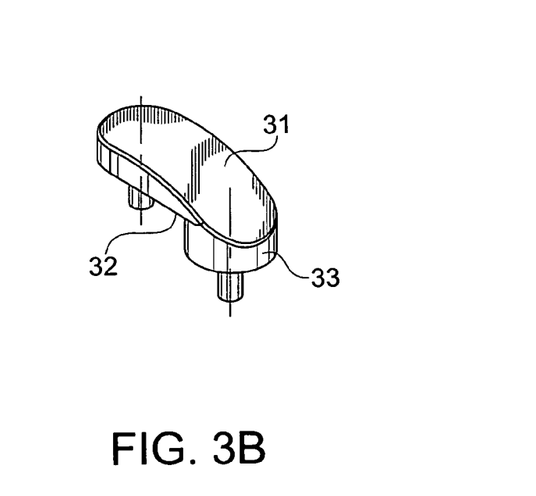

Referring to FIGS. 3A-3B, a first embodiment of a femoral component 30 includes an articulating surface 31, an underside 32, and an end 33. The articulating surface 31 is a smooth continuous surface generally shaped in the form of the femoral condyle. The underside 32 has a first portion 34 and a second portion 35, the first and the second portions 34, 35 each having a projection 36 extending therefrom. The width E of the femoral component 30 is preferably about 0.4 mm-0.63 mm. The femoral component 30 is preferably made of cobalt-chrome alloy and all surfaces of the femoral component 30 except the articulating surface 31 are coated with CP titanium plasma spray.

TABLE 1

Femoral Component

| | |
|---|---|
| Dimensions: | 10-16 mm (length) × 0.394-0.63 inches (width) × 0.765 inches (height) |
| Material: | Cast cobalt-chrome alloy |

TABLE 1-continued

Femoral Component

| | |
|---|---|
| Coating: | Coat surfaces except the first surface 31 with CP titanium plasma spray. The coating has a thickness of about 0.02 inches. |
| Projections: | 0.3 inches (length) × 0.118 inches (diameter) Distance between the two projections is about 0.587-0.82 inches |
| Second Portion: | 0.394-0.63 inches (diameter) × 0.25 inches (height) |

Figure 4:
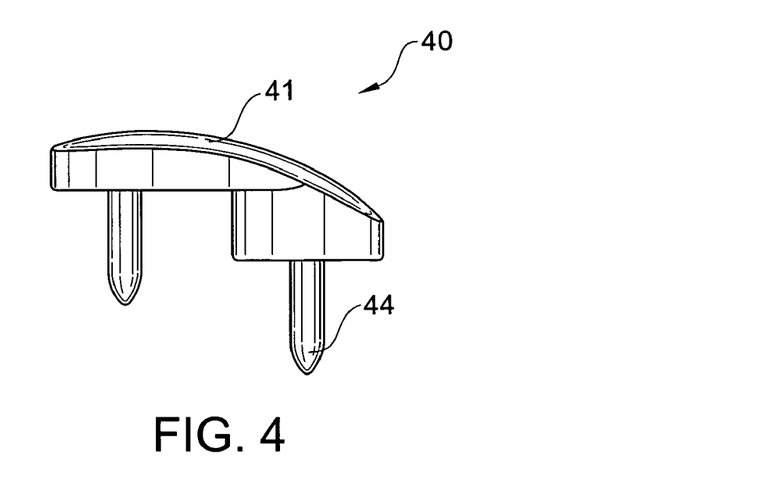
FIG. 4 illustrates an alternative femoral component of the present invention.
Figure 5:
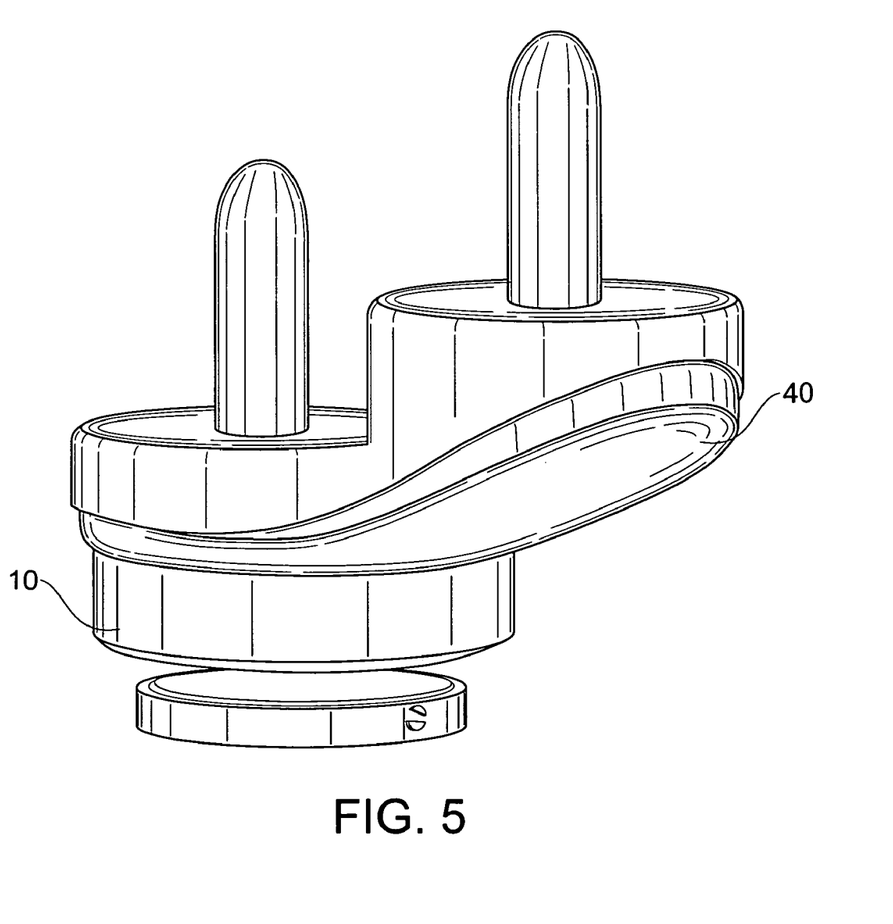
FIG. 5 illustrates the tibial component and the femoral component of the present invention, as they would contact each other in use.

Referring to FIG. 4, in another embodiment, a femoral component 40 has a top (articulating) surface 41 as in the previous embodiment, but the projections 44 from the underside are bullet tip posts. Femoral component 40 preferably has a coronal width of about 10 mm-16 mm. Femoral component 40 is preferably made of cobalt-chrome alloy with a CP titanium plasma spray coating. FIG. 5 shows the interplay between the tibial assembly 10 and the femoral component 40.

The formation of the tibial tunnel or socket may be conducted before or after the formation of a femoral trough. In an exemplary embodiment, the tibial tunnel may be formed in an antegrade manner. Alternatively, the tibia socket may be formed in a retrograde manner, by employing a retrograde drill cutter which is inserted into the joint and threaded onto the pin tip arthroscopically in a manner similar to the insertion of the retrograde drill cutter in the technique for ACL Retro-Construction by Arthrex, Inc., Naples, Fla., as disclosed in U.S. Patent Application Publication No. 2007/0233128, the disclosure of which is incorporated in its entirety by reference herein. As described and claimed in U.S. Patent Application Publication No. 2007/0233128, the retrograde insertion technique involves threading an appropriate diameter drill cutter onto an insertion post connected to a C-Ring 60 (FIG. 6A), inserting the mounted drill cutter into the knee joint through the anteromedial portal, and advancing the drill pin through a guide sleeve connected to the C-Ring 60 (FIG. 6A), through the tibia and into the joint to engage the drill cutter.

The tibial socket may be alternatively formed by employing a flip retrograde cutter 61 (FIG. 6C) having a flip cutting blade 62 that is configured to articulate between at least a first "straight" position aligned with the longitudinal axis of the cutting instrument and a second "flip" position, for example, perpendicular to the longitudinal axis of the cutting instrument. The tibial socket is formed by advancing the flip retrograde cutter 61 through the tibial and into the knee joint, flipping the blade into the second "flip" position, and then rotating the instrument while pulling back, to cut a tibial socket in a retrograde manner.

Figure 6A:
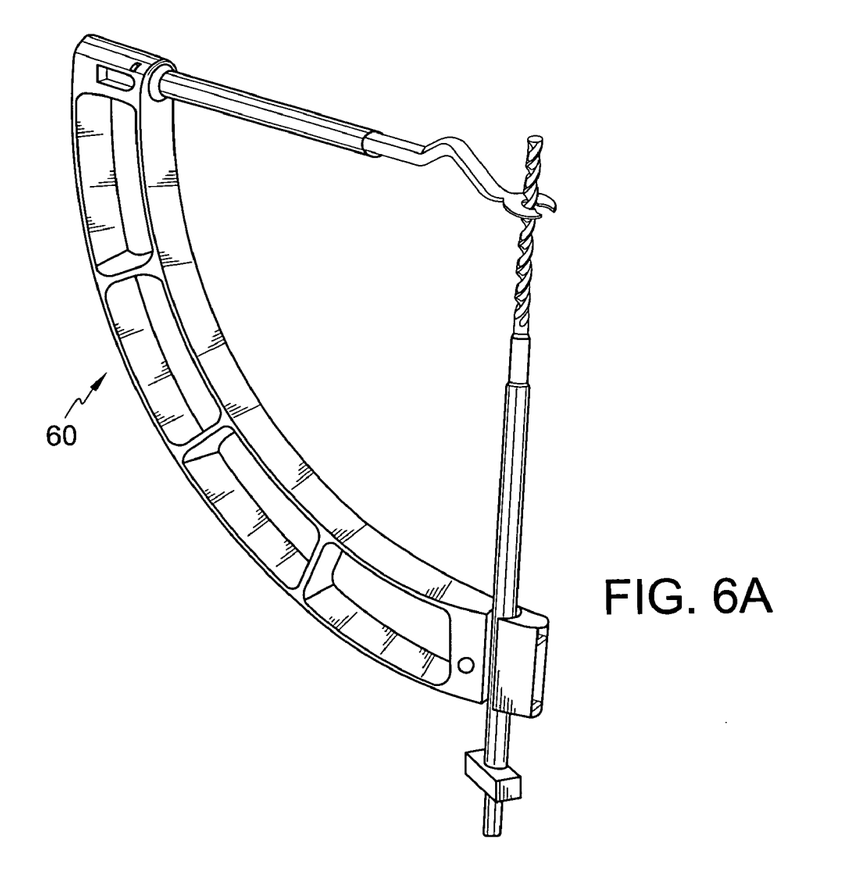
FIGS. 6A-6C illustrate a C-ring drill guide, a depth control gage, and a flip retrograde cutter, respectively, used in preparing the tibial socket.
Figure 6B:
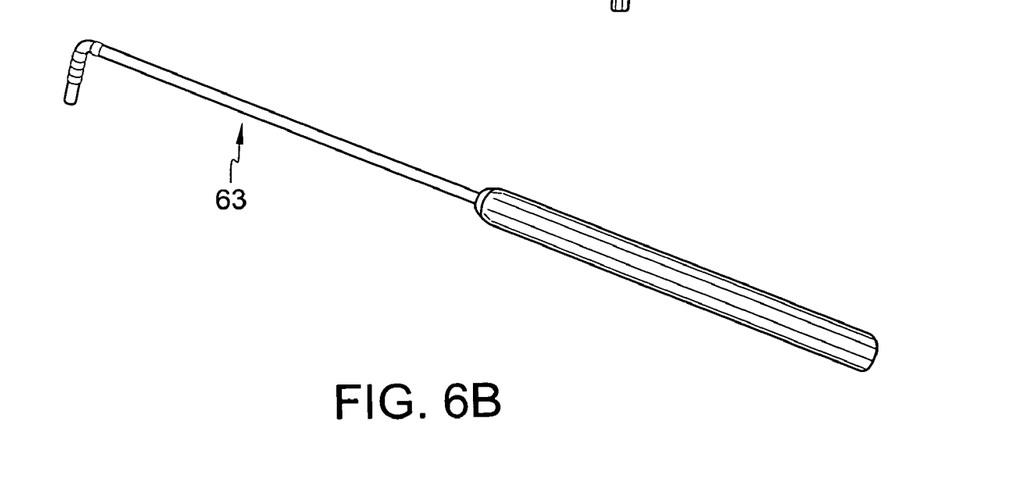
Figure 6C:
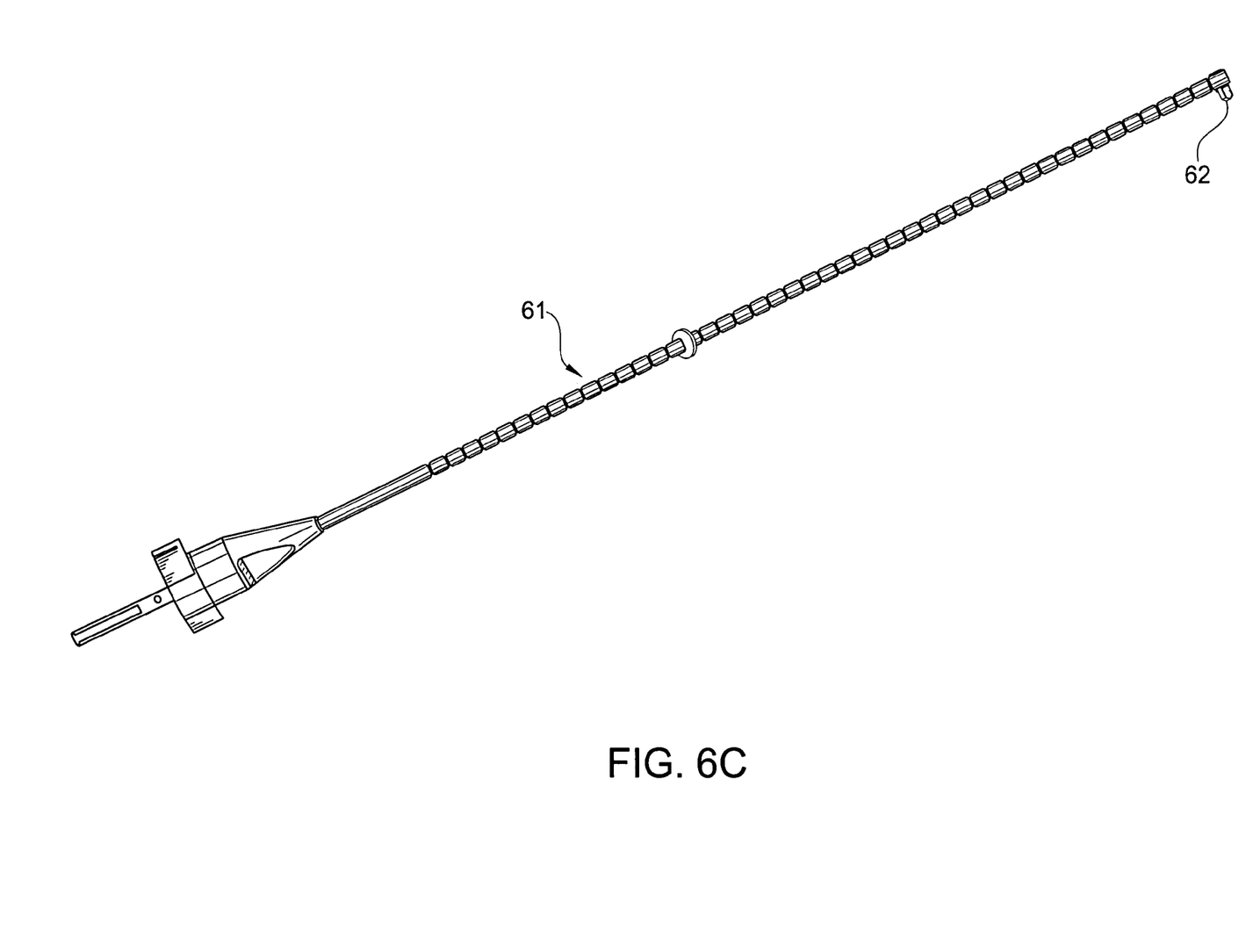
Figure 7:
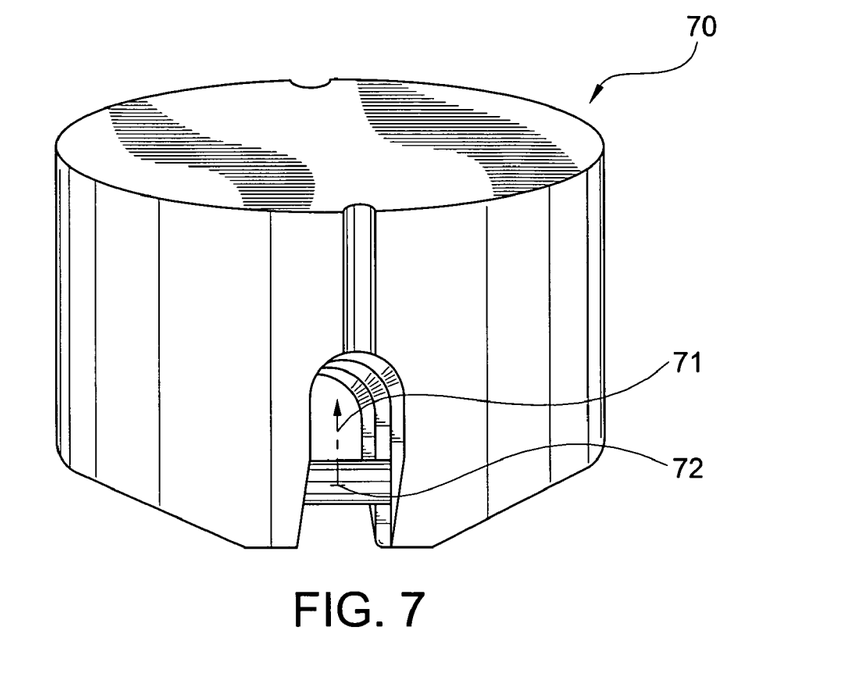
FIG. 7 illustrates a tibial trial used subsequent to the preparation of the tibial socket.

After drilling, the depth of the tibial socket may be measured using a depth gage 62 (FIG. 6b). Subsequently, a tibial trial 70 (FIG. 7) may be used to gage the tibial socket. The tibial trial 70 may have a notch 71 and a pin 72 at one end to thread a suture around the pin 72 to pull the tibial trial 70 in the tibial socket.

Referring to FIGS. 8A-8D, a femoral assembly including a template 80, a plurality of drill pins 82, 84 and a plurality of corresponding cutters 83, 85. The femoral assembly is employed to create a femoral trough on a curvature of a femoral condyle 91. The femoral trough may be formed either before or after the formation of the tibial socket.

Figure 8A:
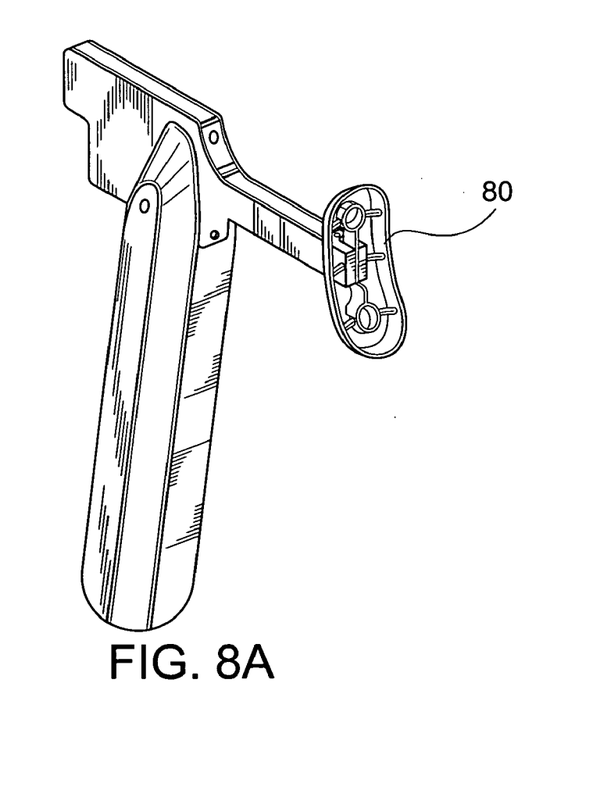
FIG. 8A illustrates the template used to create a femoral trough in the technique of the present invention.
Figure 8B:
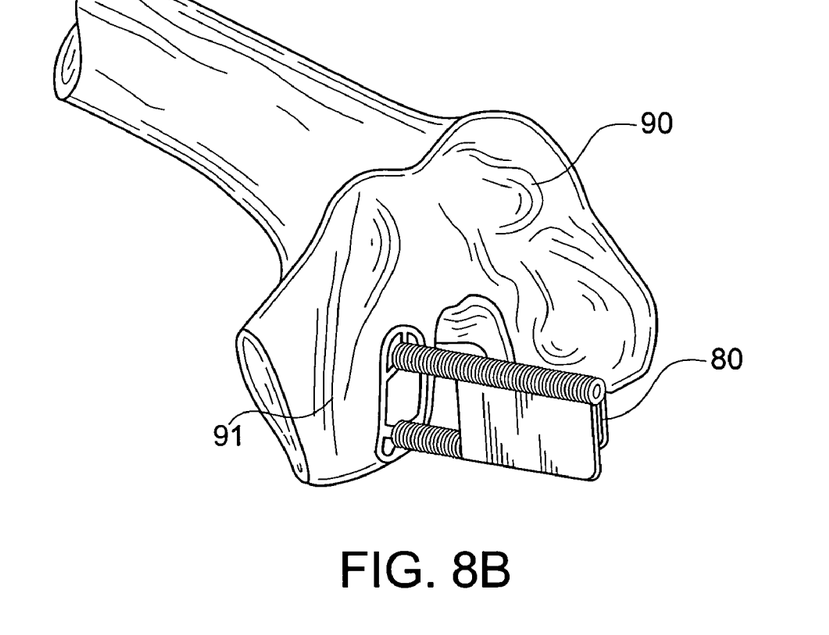
FIGS. 8B-8D illustrate the technique of creating a femoral trough in accordance with the technique of the present invention.
Figure 8C:
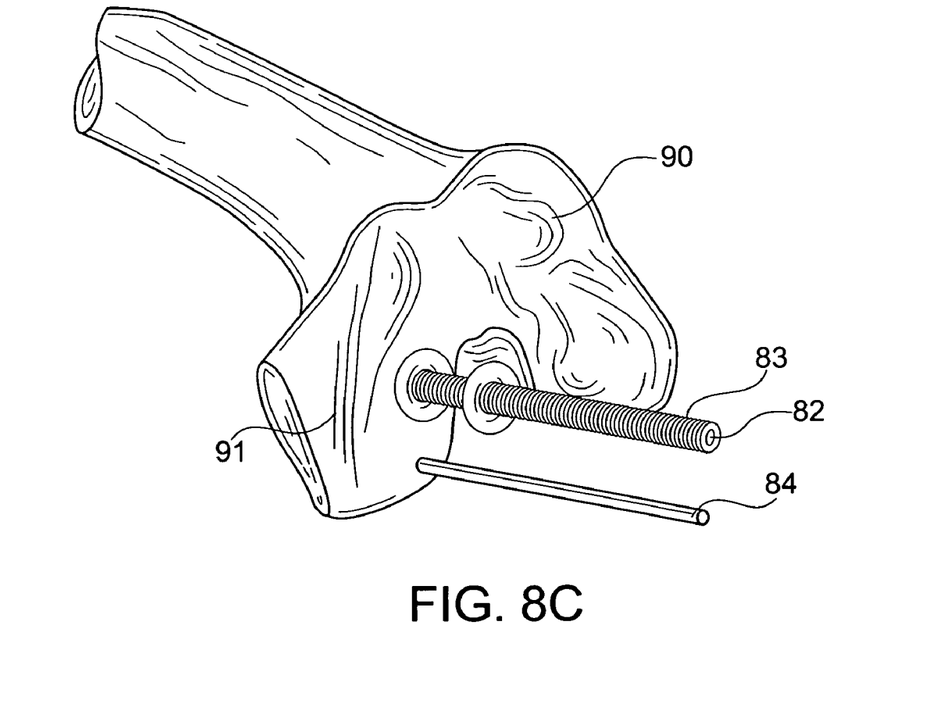
Figure 8D:
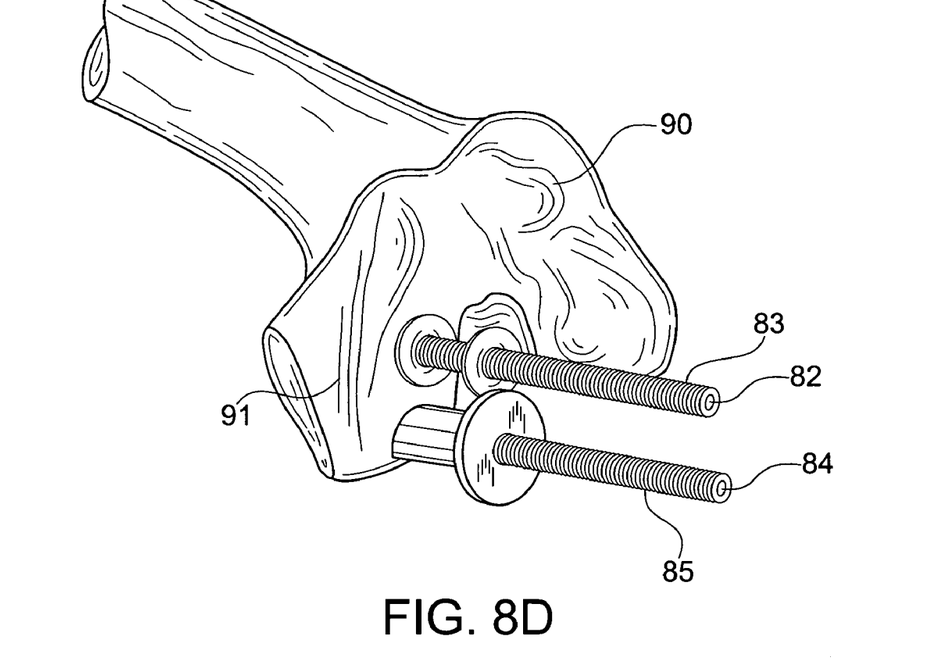
Figure 8E:
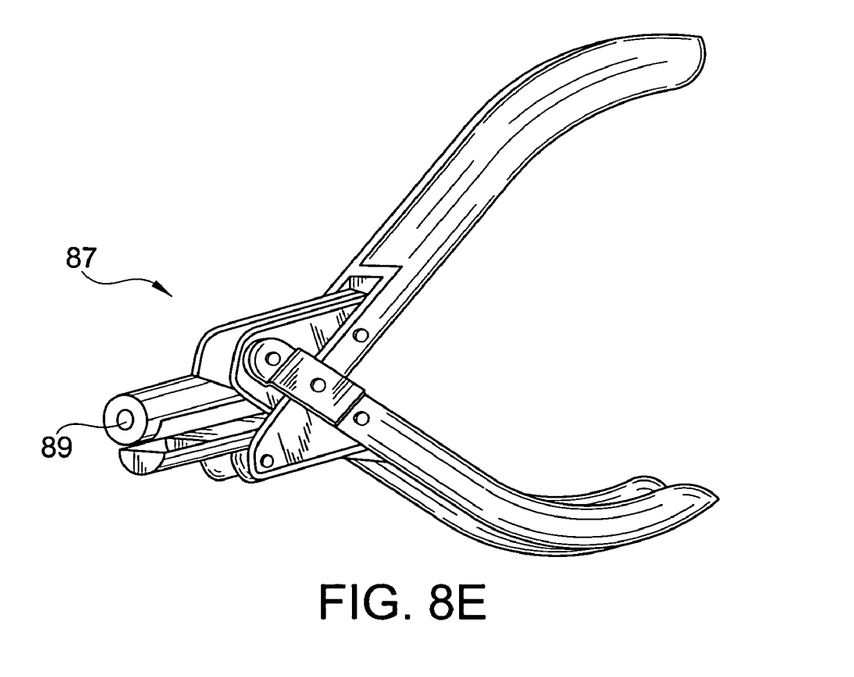
FIGS. 8E and 8F illustrate, respectively, a osteotomy plier for creating the femoral trough and a femoral impactor for inserting the femoral component into the trough.
Figure 8F:
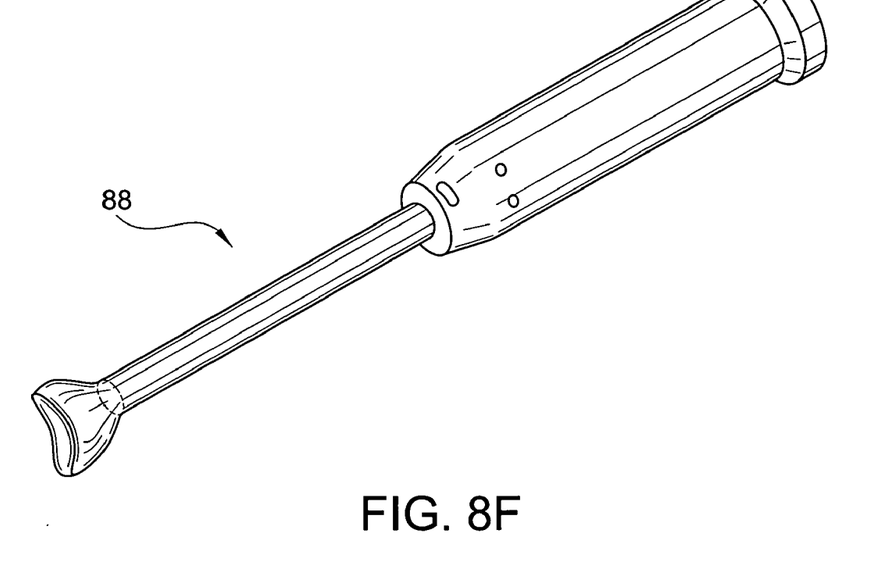

FIGS. 8B-8D illustrate a schematic view of a femur 90 with a femoral condyle 91 undergoing a method of forming a femoral trough to accept a femoral component according to the present invention. As shown in FIG. 8B, the template 80 is first aligned with the curvature of the femoral condyle 91. Next, and as illustrated in FIG. 8C, a plurality of drill pins, preferably two drill pins 82, 84, are inserted through the template 80 and drilled into the bone until the laser line on each drill pin is aligned with the end of the template 80.

Referring to FIGS. 8C and 8D, shouldered cutters 83, 85 are placed over corresponding pins 82, 84 and bored into bone until the cutters 83, 85 come in contact with the femoral condyle 91. The cutters 83, 85 may have various dimensions, for example, 12 mm or 16 mm width, to accommodate various configurations and dimensions of the curvature of the femoral condyle 91, for example, ranging from x-small to x-large.

The cutters 83, 85 are placed with depth stop over pins 82, 84 and bored until the depth stop contacts the femur. In this manner, the depth of both holes is controlled and proper seating of the femoral component is insured. The hole formed by one of the cutters is deeper than the hole made by the other one of the cutters.

After reaming the two holes in femoral condyle 91, the cutters 83, 85 are removed. The drill pin over the deeper hole is left in place and the drill pin over the shallower hole is removed. Then, an osteotomy plier 87 (FIG. 8E), with a cannulation 89, is advanced over the drill pin remaining in the femoral condyle 91. The bone between the hole created by cutters 83, 85 (which form an hourglass shaped cavity) is removed by closing the jaws of the osteotomy plier 87 using the handles of the instrument, to create an oval shaped trough.

Figure 8G:
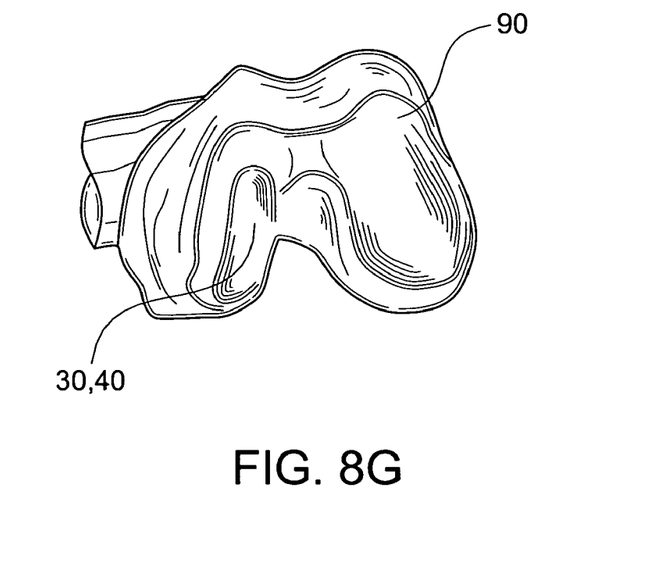
FIG. 8G illustrates a femur with the femur component inserted therein.

If desired, the fit and depth of the femoral trough may be checked. If the depth is insufficient, the above steps may be repeated using a longer shouldered cutter, for example. The femoral component 30 (FIGS. 3A-3B), 40 (FIG. 4) may be subsequently inserted by tapping it into place with a femoral impactor 88 (FIG. 8F), and the reconstructed femur 90 appears as shown in FIG. 8G.

After forming the tibial socket, the tibial component 10 (FIG. 1) is either screwed into the socket (in the case of tibial component 10 (FIG. 1)) or pulled into the tibial socket in a retrograde manner with suture (in the case of tibial component 20 (FIG. 2). Cement may be injected through the holes to prepare a mantel over which the components are placed. External guides may be used for targeting pin placement and to guide milling of sockets (angles). Femoral component 30, 40 may be cemented, press fit, and/or made be formed of one or more interlocking pieces. As stated above, tibial component 10 is screwed into the tibial socket while tibial component 20 is either press fitted or cemented. For added fixation, the femoral and/or tibial components may be secured with buttons or screws.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

We claim:

1. A method of preparing a knee joint for arthroscopic unicompartmental surgery, comprising the steps of:
    forming a tibial socket;
    forming a femoral trough, the step of forming the femoral trough comprising:
        aligning a template with the curvature of femoral condyle, and inserting two drill pins through the template and drilling into the condyle until a line marked on the outer surface of each drill pin is aligned with an end of the template;
        forming holes in the condyle by a given depth using cutters advanced over the drill pins; and
        removing bone in the condyle between the two holes using osteotomy pliers while advanced over one of the drill pins; and
    installing a femoral component in the femoral trough and a tibial component in the tibial socket.

2. The method of claim 1, wherein the cutters have a width of about 12 mm.

3. The method of claim 1, wherein the hole formed by one of the cutters is deeper than the hole formed by the other cutter.

4. The method of claim 1, wherein the femoral component has a smooth continuous articular surface shaped in the form of the femoral condyle.

5. The method of claim 1, wherein the femoral component includes a plurality of projections for securing the femoral component in the trough.

6. The method of claim 1, wherein the tibial component comprises two members and is screwed into the tibial socket.

7. The method of claim 1, wherein the tibial component comprises a single member and is pulled into the tibial socket in a retrograde manner.

* * * * *